United States Patent [19]

Danforth

[11] Patent Number: 4,822,345
[45] Date of Patent: Apr. 18, 1989

[54] CONTROLLABLE FLEXIBILITY CATHETER

[76] Inventor: John W. Danforth, 875 25th Ave., San Francisco, Calif. 94105

[21] Appl. No.: 170,596

[22] Filed: Mar. 16, 1988

Related U.S. Application Data

[63] Continuation of Ser. No. 896,471, Aug. 14, 1986, abandoned.

[51] Int. Cl.⁴ .............................................. A61M 25/00
[52] U.S. Cl. ...................................... 604/282; 604/95; 604/96; 128/348.1
[58] Field of Search ............ 604/95, 96, 103, 280–282; 128/344, 348.1

[56] References Cited

U.S. PATENT DOCUMENTS

| | | | |
|---|---|---|---|
| 1,060,665 | 5/1913 | Bell | 604/281 |
| 2,548,602 | 4/1951 | Greenburg | 128/344 X |
| 3,021,834 | 2/1962 | Sheldon | 128/6 |
| 3,470,876 | 10/1969 | Barchilon | 604/95 |
| 3,769,981 | 11/1973 | McWhorter | 604/96 |
| 3,773,034 | 11/1973 | Burns et al. | 604/95 X |
| 4,033,331 | 7/1977 | Guss et al. | 604/95 X |
| 4,141,364 | 2/1979 | Schultze | 128/344 X |
| 4,195,637 | 4/1980 | Gruntzig et al. | 128/348.1 |
| 4,215,703 | 8/1980 | Willson | 128/772 |
| 4,230,108 | 10/1980 | Young | 604/101 X |
| 4,248,234 | 2/1981 | Assenza et al. | 128/344 X |
| 4,498,473 | 2/1985 | Gereg | 604/282 |
| 4,573,470 | 3/1986 | Samson et al. | 128/344 |
| 4,582,181 | 4/1986 | Samson | 128/348.1 |
| 4,586,923 | 5/1986 | Gould et al. | 604/95 |
| 4,601,705 | 7/1986 | McCoy | 604/95 |
| 4,616,652 | 10/1986 | Simpson | 604/344 |
| 4,662,404 | 5/1987 | LeVeen et al. | 128/348.1 X |
| 4,685,473 | 8/1987 | Karcher et al. | 604/95 X |

FOREIGN PATENT DOCUMENTS

2044109 10/1980 United Kingdom.

Primary Examiner—Dalton L. Truluck
Attorney, Agent, or Firm—Townsend and Townsend

[57] ABSTRACT

A guiding catheter 40 of variable, operator-controlled flexibility to be used in the performance of a percutaneous translumenal coronary angioplasty procedure is described which includes an elongate housing 42 suitable for insertion into an artery, as well as an operator-controlled variable stiffener coupled to the distal aspect of the catheter to permit the operator performing the angioplasty procedure to increase the rigidity of the catheter. In a preferred embodiment the stiffening apparatus consists of a balloon 50 extending longitudinally along the distal end of the catheter to allow increases in rigidity of the distal end as desired by the operator. Increasing the rigidity of the guiding catheter, once installed within the coronary ostium, precludes disengagement of the guiding catheter, thus expediting the performance and enhancing the safety of the procedure.

23 Claims, 6 Drawing Sheets

CONTROLLABLE FLEXIBILITY CATHETER

This is a continuation of application Ser. No. 896,471, filed Aug. 14, 1986, now abandoned.

BACKGROUND OF THE INVENTION

1. Field of the Invention

This invention relates to catheters, and in particular, to a guiding catheter to be used in the performance of a percutaneous translumenal coronary angioplasty procedure, a guiding catheter which provides variable, operator-controlled flexibility. This feature facilitates introduction and precludes disengagement of the guiding catheter, thus expediting the performance, and enhancing the safety, of the angioplasty procedure.

2. Description of the Prior Art

In 1977 Andreas Grüntzig first used a balloon-tipped flexible catheter to percutaneously dilate a region of stenosis within the coronary artery of a patient with atherosclerotic coronary artery disease. Since that time, the incidence of percutaneous translumenal coronary angioplasty has increased exponentially. In the last several years, the performance of this procedure has become routine within most major medical centers throughout the world. Furthermore, with the advent of improved technology and increased operator skill, the indications for this procedure have also substantially increased. Concurrent with the aggressive utilization of this technique, physicians with expertise in angioplasty have been approaching increasingly difficult lesions percutaneously, and physicians with relatively little experience in angioplasty have been attempting to dilate relatively straight forward lesions with minimal formal training.

In a routine angioplasty procedure using conventional catheters, a preshaped semi-rigid guiding catheter is introduced into a peripheral artery, advanced over a guidewire along the course of the aorta and subsequently engaged within the appropriate coronary ostium. Once engaged, a second catheter (an angioplasty balloon dilation catheter), equipped with a balloon at its distal aspect and a flexible steerable guidewire, is introduced within the guiding catheter and advanced to within its distal aspect. The guidewire is then advanced within the lumen of the diseased vessel and manipulated across the region of stenosis. By rotating the guidewire, which contains a slight bend, the operator can control the course of the wire and select the appropriate lumen. Once the guidewire is positioned across the region of stenosis, the operator advances the dilation balloon over the guidewire and positions it across the stenotic lesion. The angioplasty is then accomplished by inflating the balloon to about 6-10 atmospheres of pressure. Usually three to four dilations are required for each region of stenosis, with the duration of each dilation varying between 30 to 90 seconds, depending upon anatomic considerations and operator preference. Following the final dilation, the guidewire and angioplasty balloon are withdrawn, leaving the guiding catheter in place. Coronary angiography may then be performed to evaluate the appearance of the vessel following the procedure and to determine the severity of any residual stenosis.

There are several major obstacles to the successful performance of the procedure. One major difficulty involves manipulation of the dilation balloon catheter across the region of stenosis within the appropriate coronary artery. Although the guidewire can frequently be advanced across the region with relative ease, manipulation of the balloon across the stenosis is more difficult because the catheter is substantially larger in cross section than the guidewire. Hence, relatively more resistance to the passage of this catheter within the coronary artery is commonly incurred. Merely advancing the angioplasty dilation balloon catheter against resistance often results in disengagement of the guiding catheter from the coronary ostium. Once the disengagement occurs, the angioplasty dilation balloon catheter frequently prolapses in the ascending aorta, precluding further advancement of this catheter. Inability to advance the angioplasty balloon across the stenosis because of instability of the guiding catheter and subsequent prolapse of the angioplasty balloon catheter represents one of the most common reasons for failure during the performance of a coronary angioplasty procedure. The guiding catheter disengages in this circumstance because of its flexibility. The guiding catheter has intrinsic flexibility because it must conform to the configuration of the aorta and aortic arch, which contain both linear and curved segments, during introduction. Insertion of the guiding catheter requires that it be advanced over a guidewire up the aorta, which is relatively straight, and then over the aortic arch.

One prior art solution to this difficulty was the manufacture of dilation balloon catheters designed to produce less resistance during manipulation across a stenotic lesion. It was originally proposed that these "low resistance" angioplasty dilation catheters would produce less "back pressure" and in this way preclude disengagement of the guiding catheter. Several approaches were pursued to minimize the resistance characteristics of the balloon catheters including the development of lower profile balloons (when deflated) with smooth, tapered leading edges. By itself, however, this approach did not circumvent the problem. For example, despite extensive research and development, the cross-sectional diameter of the lowest profile dilation catheter currently available is considerably greater than the corresponding diameter of the guide wires used in conventional coronary angioplasty. Hence, despite the development of these low profile dilation catheters, intracoronary resistance to the passage of these catheters remains a considerable problem. Secondly, these smaller catheters do not permit reliable transmission of intracoronary pressures and, for this reason, their use obscures vital hemodynamic monitoring on frequent occasions. And thirdly, the caliber of these low profile balloons, when inflated, is substantially smaller than the corresponding caliber of most conventional angioplasty catheters. Thus, their use frequently necessitates the installation of an intracoronary exchange wire as well as the introduction of a second (larger caliber) angioplasty dilation balloon catheter. The use of this second dilation catheter, and the necessary exchange wire, increases the time and expense of the procedure. Most significantly, the complication rate of the procedure increases as the time for, and number of, dilation balloon changes increases.

In the prior art, dislodgment of the guiding catheter was prevented by forcing the guiding catheter down the course of the vessel to be dilated or bending the guiding catheter in such a way that it "banked" off the back wall of the aorta before engaging the coronary ostium. Both techniques are particularly dangerous as they may result in dissection of the coronary artery proximal the region to be dilated.

SUMMARY OF THE INVENTION

I have developed a guiding catheter which overcomes the foregoing disadvantages of prior art catheters. My catheter allows the operator to control the flexibility of the catheter. This feature permits the operator to select the compliance characteristics which are most suitable for the particular phase of the procedure. For example, during introduction the catheter can be relatively flexible to facilitate advancement over the guidewire within the aorta, to expedite engagement of the coronary ostia, and to minimize the potential risk for catheter-induced vascular damage (a recognized complication of stiff catheters). Following engagement, the catheter can be made relatively inflexible to provide stability during the manipulation of the angioplasty dilation balloon catheter. The enhanced stability of the catheter circumvents the need for forcing the prior art relatively rigid guiding catheter deep within a coronary lumen to achieve stability, as well as the need for the sequential balloon technique. Thus, the controllable flexibility of the catheter contributes to the efficiency, as well as the safety of the procedure.

In a preferred embodiment, my catheter includes an elongate housing member having an opening extending from a proximal end to an distal end, and controllable stiffening means coupled to the elongate housing to enable control of the flexibility thereof. Optionally, a second controllable stiffener may be employed to selectively deflect a distal segment of the catheter to more accurately align the catheter with the desired artery.

The catheter of my invention is easier to install in the body and engage within the desired coronary artery, while being less traumatic to the patient. It minimizes the time for the angioplasty and precludes, in most cases, the need for sequential balloons and exchange wires.

DETAILED DESCRIPTION OF THE PREFERRED EMBODIMENTS

Figures 1, 1A, 1B:
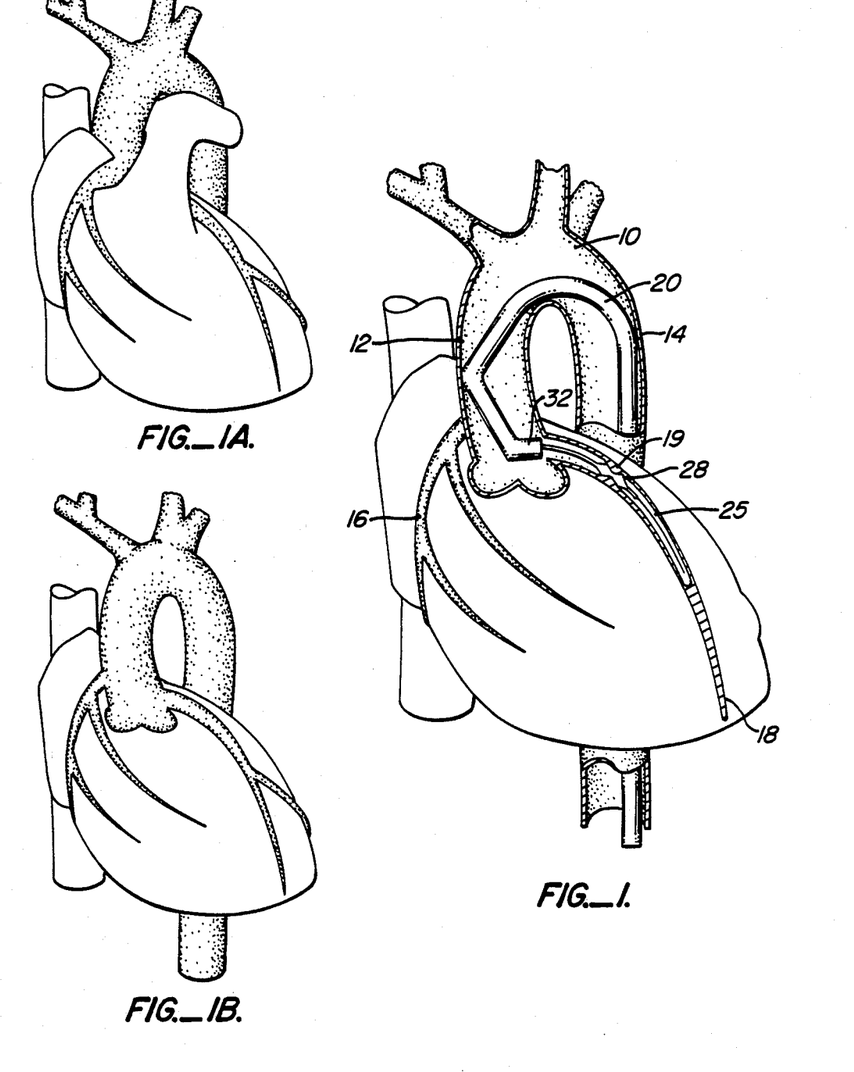
FIG. 1 is a cross-sectional view of the heart and aorta showing a stenosis in a coronary artery together with a conventional guiding catheter and dilation balloon. Two inserts have been included for the purpose of orientation.

FIG. 1 illustrates the typical configuration of a conventional left coronary guiding catheter in the aorta when engaged within the left main coronary artery during the performance of a left coronary artery 18 PTCA. (The guiding catheter has been drawn with a relatively large caliber for the purpose of clarity.) The aorta 10 includes an ascending portion 12 and a descending portion 14. The angioplasty dilation balloon 28 and intracoronary guide wire 25 have been included in FIG. 1 for the purpose of orientation. Although a left Judkin's configuration guiding catheter was selected for this, and subsequent illustrations, this discussion is not meant to be confined to this configuration alone. The concept of a variably compliant guiding catheter may be applied to all configurations of guiding catheters including the Judkin's, Sone's, Stertzer and Amplatz configurations. For the performance of an angioplasty of the right coronary artery 16, a guiding catheter with a different configuration must be employed. The concept of a variably flexible guiding catheter applies to these configurations as well.

As described above, the performance of an angioplasty initially requires the introduction of a guiding catheter within a peripheral artery. By virtue of a guidewire (not shown) and the preshaped nature of guiding catheter 20 at its distal end 32, the catheter is manipulated up the descending aorta 14 and down the ascending aorta 12 to place the end 32 of the guiding catheter 20 within the coronary ostium thus permitting subsequent advancement of the angioplasty guidewire 25 and balloon catheter 28 within the diseased vessel.

Figure 2:
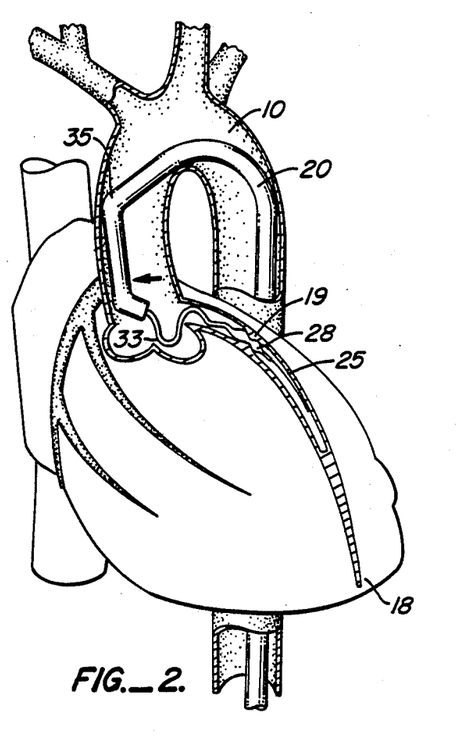
FIG. 2 is a cross section similar to FIG. 1 illustrating one disadvantage of prior art guiding catheters.

FIG. 2 illustrates a disadvantage of a guiding catheter of the prior art. The components depicted in FIG. 2 have been labeled with reference numerals corresponding to the components in FIG. 1. In FIG. 2 the dilation balloon 28 has been advanced to the region of stenosis 19. Because the resistance imparted by the lesion exceeded the compliance characteristics of the guiding catheter, however, further attempts to advance the balloon catheter resulted in disengagement of the guiding catheter 22 and prolapse of the balloon catheter. In this condition attempting to advance the balloon 28 only causes the guiding catheter to back out further, and the guidewire and inflation channel to prolapse within the ascending aorta, as shown generally by reference numeral 33.

Figure 3:
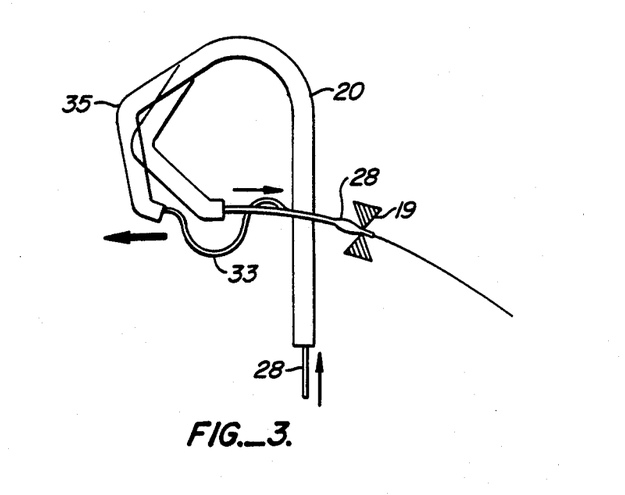
FIG. 3 illustrates the forces which develop within the guiding catheter as the angioplasty dilation balloon catheter is advanced within (in this case) the left coronary artery.

Disengagement of the guiding catheter from the coronary ostium just as the operator attempts to advance the angioplasty dilation balloon 28 across the stenosis represents one of the principal causes for failure during the course of an angioplasty procedure. The instability of the guiding catheter is believed to result from several causes. First, the catheter has intrinsic flexibility to accommodate introduction. Secondly, the material from which the catheter itself is manufactured (multiple layers of dacron webbing coated with plastic polymer) becomes more flexible as it warms to body temperature. Thirdly, the configuration of the catheter provides little or no resistance to the forces which cause it to back out. For example, as shown in FIG. 3, the application of pressure on the dilation balloon 28 for the purpose of advancing the dilation balloon across the region of stenosis increases the torque on bend 35 in guiding catheter 20, causing the angioplasty balloon catheter to prolapse in the ascending aorta precluding any further progress.

Figure 4:
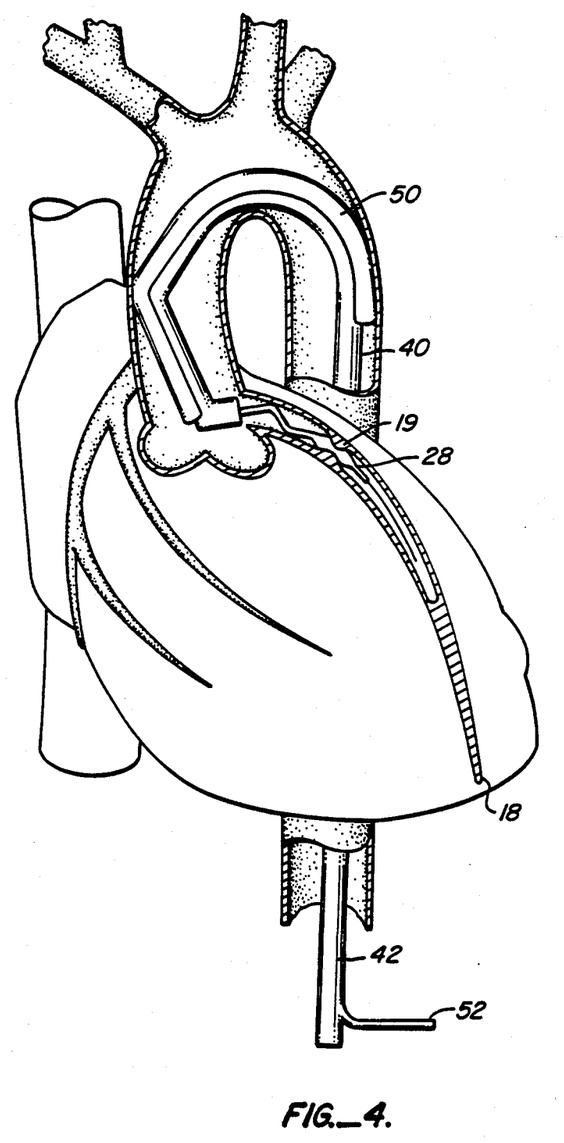
FIG. 4 is a cross section similar to FIG. 1 illustrating one embodiment of the catheter of my invention.

FIG. 4 illustrates one embodiment of the guiding catheter 40 of my invention. In contrast to prior art devices, the guiding catheter includes means for varying the flexibility of the catheter in a manner selected by the operator. For the embodiment shown in FIG. 4, the variable flexibility is provided by a balloon 50 which extends along the exterior surface of housing 42. Balloon 50 is inflatable and deflatable as desired by the operator, for example, by use of a syringe connected to a communicating channel 52 (see FIG. 6) extending through or along the catheter from exterior of the patient to the balloon 50. As also shown in FIG. 4, balloon 50, when inflated to high pressure, adds substantially to the rigidity of the distal end of catheter 40. This enables the use of additional force to advance the dilation balloon 28 through the region of stenosis. Once the dilation balloon 28 has been advanced through the region of stenosis, the balloon 50 affixed to the guiding catheter is deflated, rendering the guiding catheter 40 substantially more flexible, and hence less likely to induce any intimal vascular damage. A pressure source is then applied to inflate the balloon 28 and thereby ablate the stenosis.

My invention offers several advantages over conventional guiding catheters used in the performance of an angioplasty procedure. Present catheters, in an effort to reach a compromise between flexibility and rigidity, are generally stiff, and therefore substantially more difficult to engage within the ostium. The use of my guiding catheter with variable flexibility in its most flexible condition at the outset permits easier engagement within the coronary ostium. Once engaged, the relative inflexibility of my catheter enables it to remain engaged within the ostium in a more stable manner than conventional catheters. This stability precludes the need for multiple angioplasty catheters and exchange wires, with their associated disadvantages described above. Furthermore, the relatively inflexible catheter minimizes traumatic injury to the coronary ostium by minimizing the use of force. Disruption of the intima of the coronary ostium by conventional guiding catheters represents a well known complication of angioplasty procedures. This complication can result in a coronary occlusion, and hence, myocardial infarction. Finally, the compliance characteristics of this guiding catheter are not affected by "warming up" to body temperature.

In the embodiment depicted in FIG. 4, the balloon 50 may be filled by means of a syringe at the extracorporeal end of the catheter. Typically, the balloon will be designed to tolerate pressure on the order of 10 atmospheres. Because the catheter itself need not be as rigid as conventional catheters, the walls of the housing 42 need not be as thick. Accordingly, the caliber of the catheter with balloon 50 deflated may be less than the caliber of conventional guiding catheters. This feature will permit insertion of the catheter within a smaller arteriotomy. Furthermore, by fabricating the channel 52 connecting the exterior balloon 50 to the syringe of relatively large caliber, changes in balloon tension may be accomplished rapidly.

A further advantage of the catheter depicted in FIG. 4 is that the use of the catheter may preclude the normal requirement for two physicians. In the prior art two physicians were typically necessary, one to monitor the engagement of the guiding catheter, and one to advance the guidewire and balloon catheter. With the catheter of the depicted embodiment, a physician may advance the catheter with one hand while inflating and deflating the balloon 50 with the syringe in the other hand, thus increasing and decreasing the rigidity of the catheter as necessary to advance it.

Figures 5A, 5B:
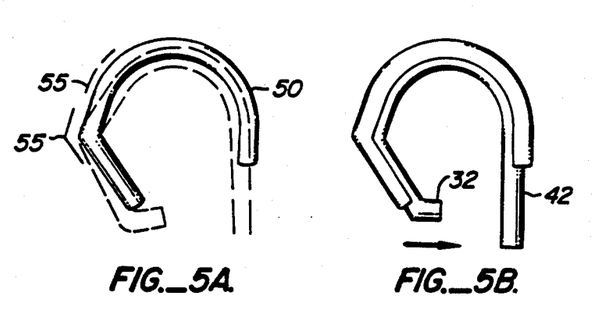
FIGS. 5A and 5B illustrates the means by which the preferred embodiment of the catheter of my invention provides additional "back pressure" to oppose the pressures described in FIG. 3.

FIG. 5 illustrates the means by which the preferred embodiment of the catheter of my invention provides additional "back pressure" to oppose the pressures described in FIG. 3. The balloon is preshaped to conform to the configuration of the guiding catheter when engaged in the coronary artery. As indicated, the arc 55 of the balloon 50, when inflated, is more acute than the corresponding arc of the distal aspect of the guiding catheter 42. As the balloon 50 is inflated, the catheter will begin to assume the configuration of the preshaped balloon 50. This will result in enhanced "back pressure" and thus enhanced stability of the guiding catheter during advancement of the angioplasty dilation balloon catheter 30.

Figure 6:
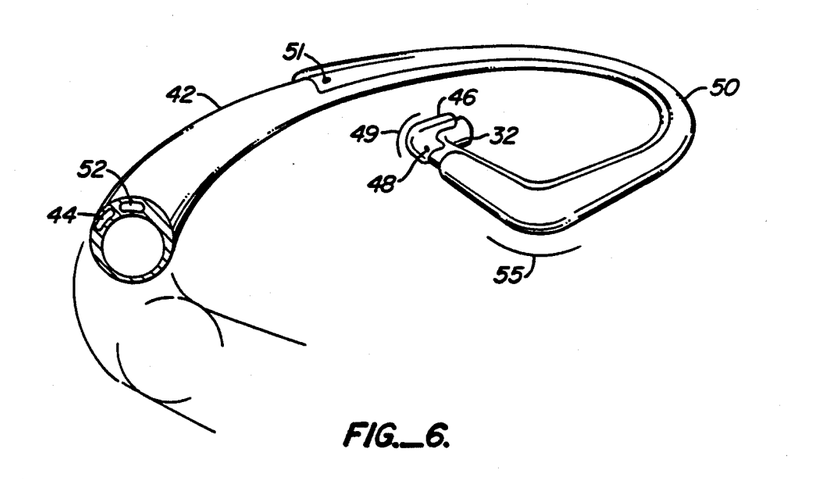
FIG. 6 is a perspective view of the catheter shown in FIG. 4.
Figure 7:
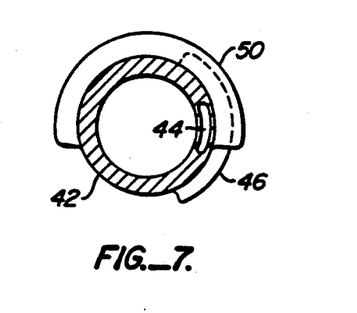
FIG. 7 is a cross section of the distal end of the catheter shown FIG. 4.

FIG. 6 is an expanded view of the distal end of the catheter showing housing 42 and balloon 50 in further detail. A cross section of the catheter is also depicted. Communicating channel 52, also contained within the catheter, connects to balloon 50 through lumen 51 to allow pressurization. FIG. 7 is a cross section of the distal end of the catheter showing balloon 50.

FIG. 6 also illustrates an optional feature of my catheter. In this embodiment a second external balloon 46 is provided which is coupled to communicating channel 44 by lumen 48. In the same manner as balloon 50, balloon 46 may be inflated from outside the patient. Secondary balloon 46 enables selective deflection of the distal end of catheter 40 to assist in positioning the catheter within the coronary artery. By placing the secondary balloon on catheter 40 at 90° rotation from the preshaped curve 49 (and from the orientation of balloon 50), the distal end of the catheter may be deflected anteriorly or posteriorly to aid subselective cannulization of the LAD and circumflex branches of the left coronary system.

Figure 8A:
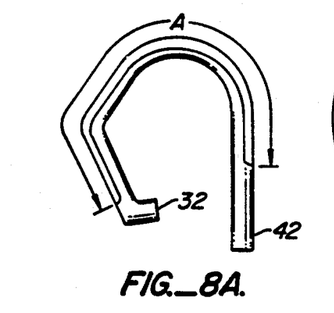
FIGS. 8A and 8B illustrates another approach to the preferred embodiment.
Figure 8B:
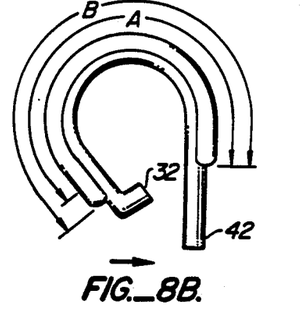

FIG. 8 illustrates another approach to bonding the balloon 50 to the catheter housing 42. In this embodiment, the balloon is composed of an elastic material that permits elongation of the balloon with inflation to high pressures. In this embodiment, the preshaped configuration of the balloon is less important than in the embodiment described in FIG. 5. Since the balloon is attached to the circumferential aspect of the distal end of the guiding catheter, and since the balloon elongates with progressive inflation, the application of enhanced inflation pressure will change the configuration of the guiding catheter, providing enhanced "back pressure."

Figures 9A, 9B:
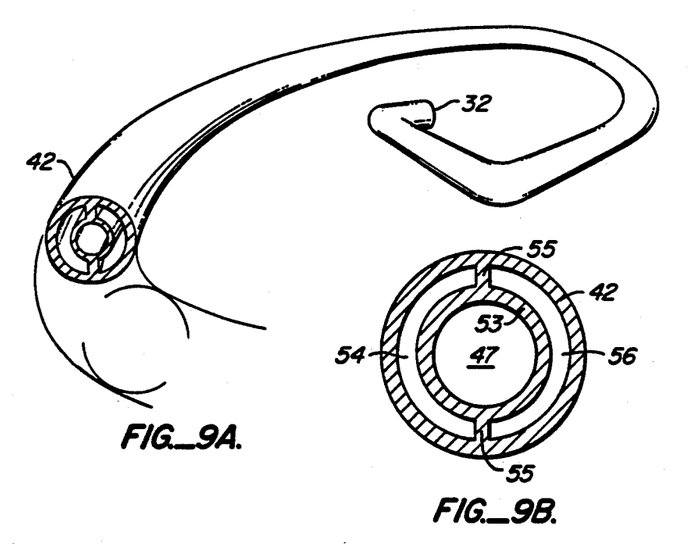
FIGS. 9A and 9B depicts another embodiment of the catheter having variable flexibility by virtue of channels for carrying iced saline.
Figures 10A, 10B:
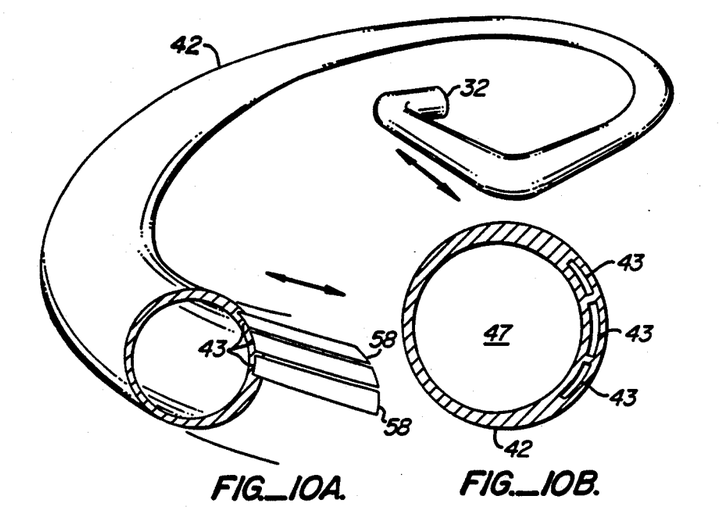
FIGS. 10A, 10B, 10C, 10D and 10E depicts another embodiment of a variable flexibility catheter which permits the introduction of stiff wires of tensionable members.
Figure 10C:
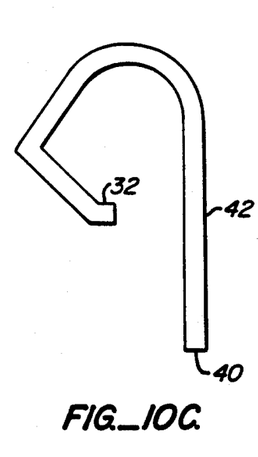
Figure 10D:
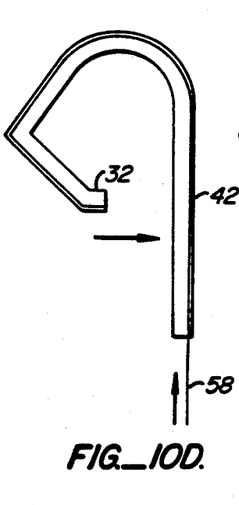
Figure 10E:
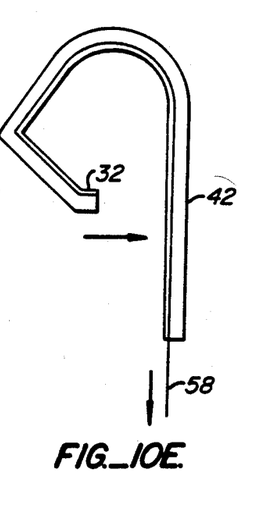

FIG. 9 illustrates another embodiment of my invention in which the stiffness of the catheter is imparted by the introduction of iced saline solution or other coolant. In this embodiment an additional tube 53 surrounds the interior channel 47 (through which the angioplasty dilation catheter is passed) to provide two or more openings 54, 56 between housing 42 and tube 53. Inner channel 53 is coupled to outer housing 42 at least at two locations 55 to thereby provide a first chamber 54 and a second chamber 56. By circulating iced saline into one of the chambers 54 and 56 and out the other, and/or by manufacturing housing 42 from material which is temperature sensitive, the rigidity of the catheter may be substantially increased as necessary.

In another embodiment of my invention, the rigidity of the catheter can be enhanced by the insertion of relatively stiff wires through channels along the periphery of the catheter. This embodiment is shown in FIG. 10. As shown, the housing 42 includes several integral channels 43 to permit insertion of one or more relatively stiff wires 58 along the periphery of the catheter. By bending the wires into the desired configuration and then inserting them after the catheter has been properly positioned, the wires 58 will add to the stiffness of the catheter. As before, the chamber 47 for the dilation balloon catheter is disposed within housing 42. In a further embodiment of my invention, instead of using stiff wires, relatively flexible wires are positioned around the periphery of the housing 42 and then tension applied to them after the catheter is properly positioned to increase the rigidity of the catheter. In such an embodiment, wires 58 are affixed to the distal end of the catheter. Of course, it is not essential that individual pockets for the wires 58 be employed, rather a conventional housing may be chosen and the wires simply inserted within chamber 47.

In other embodiments of my invention, other means for stiffening the catheter may also be employed. For example, wires 58 may be fabricated from memory alloys or bimetal thermocouples which are then heated or cooled to the desired temperature by circulation of fluid through the catheter. In such an embodiment, the wires will be relatively flexible at body temperature, and then caused to assume a desired shape by either being cooled to a lower temperature, or heated to a higher temperature.

In still further embodiments of my catheter, the guiding catheter is fabricated from material having properties which change when subjected to light, ultrasound, radio frequency, magnetic fields or other penetrating forces such as electric current. A laser, ultrasound source, etc., is then employed once the catheter is properly positioned to increase its rigidity.

The foregoing has been a description of the preferred embodiments of the invention. Although many specific details have been described, it should be understood that the description is only for the purposes of explaining the invention, and not limiting it. It should be further understood that the configuration of the catheter proposed herein is not limited to the left Jodkin's configuration alone. This configuration was selected for the purpose of illustration only. The scope of the invention may be ascertained from the appended claims.

I claim:

1. A catheter comprising:
    an elongate housing having an opening extending from a proximal end to a distal end of its length, the housing adapted to be inserted into a vessel wherein said housing, when inserted in the vessel, has a first substantially curved portion and a second substantially straight portion, said first portion being more proximate to the distal end than said second portion; and
    controllable stiffening means coupled to said first portion of the length of the elongated housing to provide at least a first higher flexibility of said first portion of the elongated housing and a second lower flexibility of said first portion of the elongated housing as selected by a user of the catheter,
    wherein the flexibility of said second portion of said elongate housing is substantially unchanged by said user-selected change in flexibility of said first portion of said elongated housing, and wherein the curvature of said curved portion is not substantially decreased when said housing has said second lower flexibility.

2. A catheter as in claim 1 wherein the controllable stiffening means comprises a longitudinally-extending primary balloon disposed along said first portion of the elongate housing.

3. A catheter as in claim 2 further comprising an enclosed channel extending adjacent the opening of the elongate housing and coupled to the balloon to permit inflation thereof.

4. A catheter as in claim 3 wherein the channel extends from the proximal end to the primary balloon.

5. A catheter as in claim 2 wherein a wall of the balloon comprises a first region of the exterior surface of said first portion of the elongate housing.

6. A catheter as in claim 2 wherein the balloon is disposed around only a selected part of the cross sectional circumference of the exterior surface of said first portion of the elongate housing, wherein the curvature of said second portion when said balloon is uninflated is less than the curvature of said second portion when the balloon is inflated.

7. A catheter as in claim 1 wherein the controllable stiffening means comprises at least one wire to be inserted into the elongate housing, the wire having been previously bent to have a desired configuration along a selected part of its length corresponding to said first portion of the length of the elongate housing.

8. A catheter as in claim 1 wherein the controllable stiffening means comprises a channel eccentrically disposed along said first portion of the housing for containing fluid.

9. A catheter comprising:
    an elongate housing having an opening extending from a proximal end to a distal end of its length, the housing adapted to be inserted into a vessel;
    controllable stiffening means comprising a longitudinally extending primary balloon coupled to a portion of the length of the elongate housing to provide at least a first higher flexibility of that portion of the elongate housing and a second lower flexibility of that portion of the elongate housing as selected by a user of the catheter; and
    a secondary balloon disposed along the elongate housing more proximal to the distal end than the primary balloon.

10. A catheter as in claim 9 further comprising a secondary channel extending adjacent the opening of the elongate housing and coupled to the secondary balloon to permit inflation thereof.

11. A catheter as in claim 10 wherein a wall of the secondary balloon comprises a second region of the exterior surface of the elongate housing.

12. A catheter as in claim 11 wherein the secondary balloon is positioned axially offset from the primary balloon.

13. A catheter comprising:
    an elongate housing having an opening extending from a proximal end to a distal end of its length, the housing adapted to be inserted into a vessel;
    controllable stiffening means coupled to a portion of the length of the elongate housing to provide at least a first higher flexibility of that portion of the elongate housing and a second lower flexibility of that portion of the elongate housing as selected by a user of the catheter; and
    an angioplasty dilation catheter disposed within the opening.

14. A guiding catheter for use in angioplasty comprising:
  an elongate tube having an opening therethrough extending from a proximal end to a distal end, the tube adapted to be inserted into a vascular member; and
  controllable stiffening means coupled to a surface of the elongate tube along a first non-linear portion of its length, said stiffening means being substantially uncoupled along a second portion of the length of the tube, said first portion being more proximate to the distal end than said second portion, said stiffening means being adapted to allow said first portion of the elongate tube to which the controllable stiffening means is coupled to be made more rigid at selected times, without substantially affecting the flexibility of said second portion, and wherein the tube and a guidewire may be introduced into a vesicular member in a first less rigid state, then changed to a second more rigid state to facilitate introduction of an angioplasty dilation balloon catheter across a region of coronary stenosis.

15. A method for performing an angioplasty procedure using a guiding catheter having controllable stiffening means affixed to a portion of the catheter in proximity to the distal end comprising:
  introducing the guiding catheter to a desired position within a patient;
  employing the controllable stiffening means to increase the rigidity of the portion of the catheter to which the controllable stiffening means is affixed;
  performing the angioplasty procedure;
  employing the controllable stiffening means to reduce the rigidity of the portion of the catheter; and removing the catheter.

16. A catheter as in claim 14 wherein the second more rigid state places the catheter in a configuration which is more highly bent than when the catheter is in the first less rigid state.

17. A catheter as in claim 14 wherein the second more rigid state places the catheter in a configuration adapted for maintaining the catheter in a position suitable for the performance of coronary angioplasty.

18. A catheter as in claim 1 wherein said first portion of the length comprises a region in closer proximity to the distal end than to the proximal end.

19. A catheter as in claim 2 wherein the primary balloon is eccentrically disposed along said first portion of the elongate housing.

20. A catheter as in claim 1 wherein the controllable stiffening means comprises at least one tensionable element secured to the distal end and disposed within a channel in the elongate housing.

21. A method as claimed in claim 15 further comprising:
  employing the controllable stiffening means to position the distal end of the guiding catheter for alignment in the coronary ostium.

22. A method as claimed in claim 15 further comprising:
  continuously varying the rigidity of a portion of the catheter during said performance of the angioplasty procedure.

23. A guiding catheter for use in angioplasty comprising:
  an elongate tube having an opening therethrough extending from a proximal end to a distal end, the tube adapted to be inserted into a vascular member; and
  controllable stiffening means coupled to a surface of the elongate tube along a first non-linear portion of its length, said stiffening means being substantially uncoupled along a second portion of a length of the tube, said stiffening means being adapted to allow said first portion of the elongate tube to which the controllable stiffening means is coupled to be more rigid at selected times, without substantially affecting the flexibility of said second portion, and wherein the controllable stiffening means is effective to position the distal end of said elongate tube for alignment in the coronary ostium.

* * * * *